(12) United States Patent
Pottathil et al.

(10) Patent No.: US 9,023,625 B2
(45) Date of Patent: May 5, 2015

(54) METHODS FOR PRODUCTION OF ALGAE DERIVED OILS

(75) Inventors: Raveendran Pottathil, La Jolla, CA (US); Sanjay Kumar Amrutrao Deshmukh, Maharashtra (IN)

(73) Assignee: IO-Mega Holding Corporation, Satellite Beach, FL (US)

( * ) Notice: Subject to any disclaimer, the term of this patent is extended or adjusted under 35 U.S.C. 154(b) by 0 days.

(21) Appl. No.: 13/704,193

(22) PCT Filed: Jun. 14, 2011

(86) PCT No.: PCT/US2011/040320
§ 371 (c)(1),
(2), (4) Date: Feb. 20, 2013

(87) PCT Pub. No.: WO2011/159682
PCT Pub. Date: Dec. 22, 2011

(65) Prior Publication Data
US 2013/0210093 A1 Aug. 15, 2013

Related U.S. Application Data

(60) Provisional application No. 61/354,367, filed on Jun. 14, 2010.

(51) Int. Cl.
*C12P 7/64* (2006.01)
*C12N 1/12* (2006.01)
*A01G 33/00* (2006.01)

(52) U.S. Cl.
CPC .............. *C12P 7/6427* (2013.01); *A01G 33/00* (2013.01); *C12N 1/12* (2013.01)

(58) Field of Classification Search
None
See application file for complete search history.

(56) References Cited

U.S. PATENT DOCUMENTS

| | | | |
|---|---|---|---|
| 5,130,242 A * | 7/1992 | Barclay | 435/134 |
| 5,244,921 A | 9/1993 | Kyle et al. | |
| 5,340,742 A | 8/1994 | Barclay | |
| 5,407,957 A | 4/1995 | Kyle et al. | |
| 5,492,938 A * | 2/1996 | Kyle et al. | 514/786 |
| 5,518,918 A | 5/1996 | Barclay | |
| 5,583,019 A | 12/1996 | Barclay | |
| 5,658,767 A | 8/1997 | Kyle | |
| 5,711,983 A | 1/1998 | Kyle et al. | |
| 6,166,231 A | 12/2000 | Hoeksema | |
| 6,319,698 B1 | 11/2001 | Barclay | |
| 6,372,460 B1 | 4/2002 | Gladue et al. | |
| 6,451,567 B1 | 9/2002 | Barclay | |
| 6,566,123 B1 | 5/2003 | Barclay | |
| 6,607,900 B2 | 8/2003 | Bailey et al. | |
| 6,750,048 B2 | 6/2004 | Ruecker et al. | |
| 7,005,280 B2 | 2/2006 | Barclay | |
| 7,011,962 B2 | 3/2006 | Barclay | |
| 7,163,811 B2 | 1/2007 | Behrens et al. | |
| 7,252,979 B2 | 8/2007 | Behrens et al. | |
| 7,351,558 B2 | 4/2008 | Ruecker et al. | |
| 7,381,558 B2 | 6/2008 | Barclay | |
| 7,419,596 B2 | 9/2008 | Dueppen et al. | |
| 7,566,570 B2 | 7/2009 | Abril | |
| 7,579,174 B2 | 8/2009 | Bailey et al. | |
| 7,601,523 B2 | 10/2009 | Barclay | |
| 7,662,598 B2 | 2/2010 | Ruecker et al. | |
| 7,678,931 B2 | 3/2010 | Fichtali et al. | |
| 7,695,626 B2 | 4/2010 | Dueppen et al. | |
| 7,732,170 B2 | 6/2010 | Bailey et al. | |
| 2001/0000151 A1 | 4/2001 | Barclay | |
| 2001/0016218 A1 | 8/2001 | Barclay | |
| 2001/0046691 A1 | 11/2001 | Bailey et al. | |
| 2002/0001833 A1 | 1/2002 | Ruecker et al. | |
| 2002/0037561 A1 | 3/2002 | Barclay | |
| 2002/0123111 A1 | 9/2002 | Gladue et al. | |
| 2003/0100097 A1 | 5/2003 | Barclay | |
| 2003/0138477 A1 | 7/2003 | Barclay | |
| 2003/0180898 A1 | 9/2003 | Bailey et al. | |
| 2004/0203121 A1 | 10/2004 | Barclay | |
| 2004/0219648 A1 | 11/2004 | Barclay | |
| 2004/0229325 A1 | 11/2004 | Ruecker et al. | |
| 2005/0112736 A1 | 5/2005 | Behrens et al. | |
| 2005/0115897 A1 | 6/2005 | Dueppen et al. | |
| 2005/0129739 A1 | 6/2005 | Kohn et al. | |
| 2005/0170479 A1 | 8/2005 | Weaver et al. | |
| 2005/0215803 A1 | 9/2005 | Abril | |
| 2006/0094089 A1 | 5/2006 | Barclay | |
| 2006/0099693 A1 | 5/2006 | Kobzeff et al. | |
| 2006/0100279 A1 | 5/2006 | Behrens et al. | |
| 2006/0122410 A1 | 6/2006 | Fichtali et al. | |
| 2006/0160203 A1 | 7/2006 | Barclay | |

(Continued)

FOREIGN PATENT DOCUMENTS

| WO | WO9107498 A1 | 5/1991 |
|---|---|---|
| WO | WO9111918 A1 | 8/1991 |

(Continued)

OTHER PUBLICATIONS

Report by "Cornucopia Institute": "Organic Infant Formula Ingredients Processed with Toxic Chemical", Apr. 14, 2008; pp. 1-3; web page http://www.cornucopia.org/2008/04.*
"Wastewater Treatment and Resource Recovery", Report of workshop on high-rate algae ponds, Singapore, Feb. 1980, pp. 1-47.*
Grima et al. "Comparison between extraction of lipids and fatty acids from microalgal biomass". JAOCS, 1994, vol. 71, No. 9, pp. 955-959.*
Kris-Etherton et al., Arteriosclerosis, Thrombosis, and Vascular Biology, 2003;23:151-152.
Ruxton et al., Journal of Human Nutrition and Dietetics vol. 17, Issue 5, pp. 449-459, Oct. 2004.

(Continued)

*Primary Examiner* — Vera Afremova
(74) *Attorney, Agent, or Firm* — Foley & Lardner LLP

(57) ABSTRACT

The present invention comprises a method of producing algae derived oils comprising growing, stressing, and harvesting algae and then extracting total lipids from which specific oil fractions are purified.

11 Claims, 3 Drawing Sheets

(56) References Cited

U.S. PATENT DOCUMENTS

| | | |
|---|---|---|
| 2006/0177920 A1 | 8/2006 | Barclay |
| 2006/0188969 A1 | 8/2006 | Barclay |
| 2006/0286205 A1 | 12/2006 | Fichtali et al. |
| 2006/0286648 A1 | 12/2006 | Bailey et al. |
| 2006/0286649 A1 | 12/2006 | Bailey et al. |
| 2007/0004678 A1 | 1/2007 | Kohn et al. |
| 2007/0026050 A1 | 2/2007 | Barclay |
| 2007/0082384 A1 | 4/2007 | Barclay |
| 2008/0032352 A1 | 2/2008 | Behrens et al. |
| 2008/0032353 A1 | 2/2008 | Behrens et al. |
| 2008/0032354 A1 | 2/2008 | Behrens et al. |
| 2008/0032355 A1 | 2/2008 | Behrens et al. |
| 2008/0032356 A1 | 2/2008 | Behrens et al. |
| 2008/0032357 A1 | 2/2008 | Behrens et al. |
| 2008/0032358 A1 | 2/2008 | Behrens et al. |
| 2008/0032359 A1 | 2/2008 | Behrens et al. |
| 2008/0032360 A1 | 2/2008 | Bailey et al. |
| 2008/0032361 A1 | 2/2008 | Bailey et al. |
| 2008/0032362 A1 | 2/2008 | Bailey et al. |
| 2008/0032363 A1 | 2/2008 | Bailey et al. |
| 2008/0032364 A1 | 2/2008 | Bailey et al. |
| 2008/0032365 A1 | 2/2008 | Bailey et al. |
| 2008/0032366 A1 | 2/2008 | Bailey et al. |
| 2008/0032381 A1 | 2/2008 | Bailey et al. |
| 2008/0032387 A1 | 2/2008 | Bailey et al. |
| 2008/0038800 A1 | 2/2008 | Ruecker et al. |
| 2008/0044388 A1 | 2/2008 | Barclay |
| 2008/0044389 A1 | 2/2008 | Barclay |
| 2008/0044865 A1 | 2/2008 | Behrens et al. |
| 2008/0044866 A1 | 2/2008 | Behrens et al. |
| 2008/0044875 A1 | 2/2008 | Ruecker et al. |
| 2008/0044876 A1 | 2/2008 | Ruecker et al. |
| 2008/0057551 A1 | 3/2008 | Bailey et al. |
| 2008/0166780 A1 | 7/2008 | Barclay |
| 2008/0199923 A1 | 8/2008 | Barclay |
| 2008/0312468 A1 | 12/2008 | Fleisher |
| 2009/0023808 A1 | 1/2009 | Raman et al. |
| 2009/0064567 A1 * | 3/2009 | Lippmeier et al. ............. 44/308 |
| 2009/0099379 A1 | 4/2009 | Dueppen et al. |
| 2009/0227678 A1 | 9/2009 | Bijl et al. |
| 2010/0145085 A1 | 6/2010 | Abril |

FOREIGN PATENT DOCUMENTS

| | | |
|---|---|---|
| WO | WO9114427 A1 | 10/1991 |
| WO | WO9213086 A1 | 8/1992 |
| WO | WO9222291 A1 | 12/1992 |
| WO | WO9408467 A1 | 4/1994 |
| WO | WO9621037 A1 | 7/1996 |
| WO | WO9906585 A1 | 2/1999 |
| WO | WO0036059 A1 | 6/2000 |
| WO | WO0153512 A1 | 7/2001 |
| WO | WO0154510 A1 | 8/2001 |
| WO | WO02092073 A1 | 11/2002 |
| WO | WO02092540 A1 | 11/2002 |
| WO | WO03049832 A1 | 6/2003 |
| WO | WO03092628 A2 | 11/2003 |
| WO | WO2005035775 A1 | 4/2005 |
| WO | WO2005072477 A2 | 8/2005 |
| WO | WO2006046943 A2 | 5/2006 |
| WO | WO2006047445 A2 | 5/2006 |
| WO | WO2006124598 A2 | 11/2006 |
| WO | WO2006136539 A1 | 12/2006 |
| WO | WO2009006317 A1 | 1/2009 |
| WO | WO2009035551 A1 | 3/2009 |
| WO | WO2009094440 A1 | 7/2009 |

OTHER PUBLICATIONS

Mar. 2010 Frost and Sullivan report, "Strategic Analysis of the North American Marine and Algae Oil Omega-3 Ingredients Market".
Barclay et al., Journal of Applied Phycology, vol. 6, No. 2, 123-129.
Ward et al., Appl. Environ. Microbio., Feb. 1991 p. 419-425.
Reitan et al., J. Phycology, Dec. 1994, vol. 30, Issue 6, pp. 972-979.
You et al., J. Hazardous Mater., Dec. 15, 2009; 172 (1):38-45.
Follegatti-Romero et al., J. of Supercritical Fluids, Jul. 2009; 49 (3):323-329.

* cited by examiner

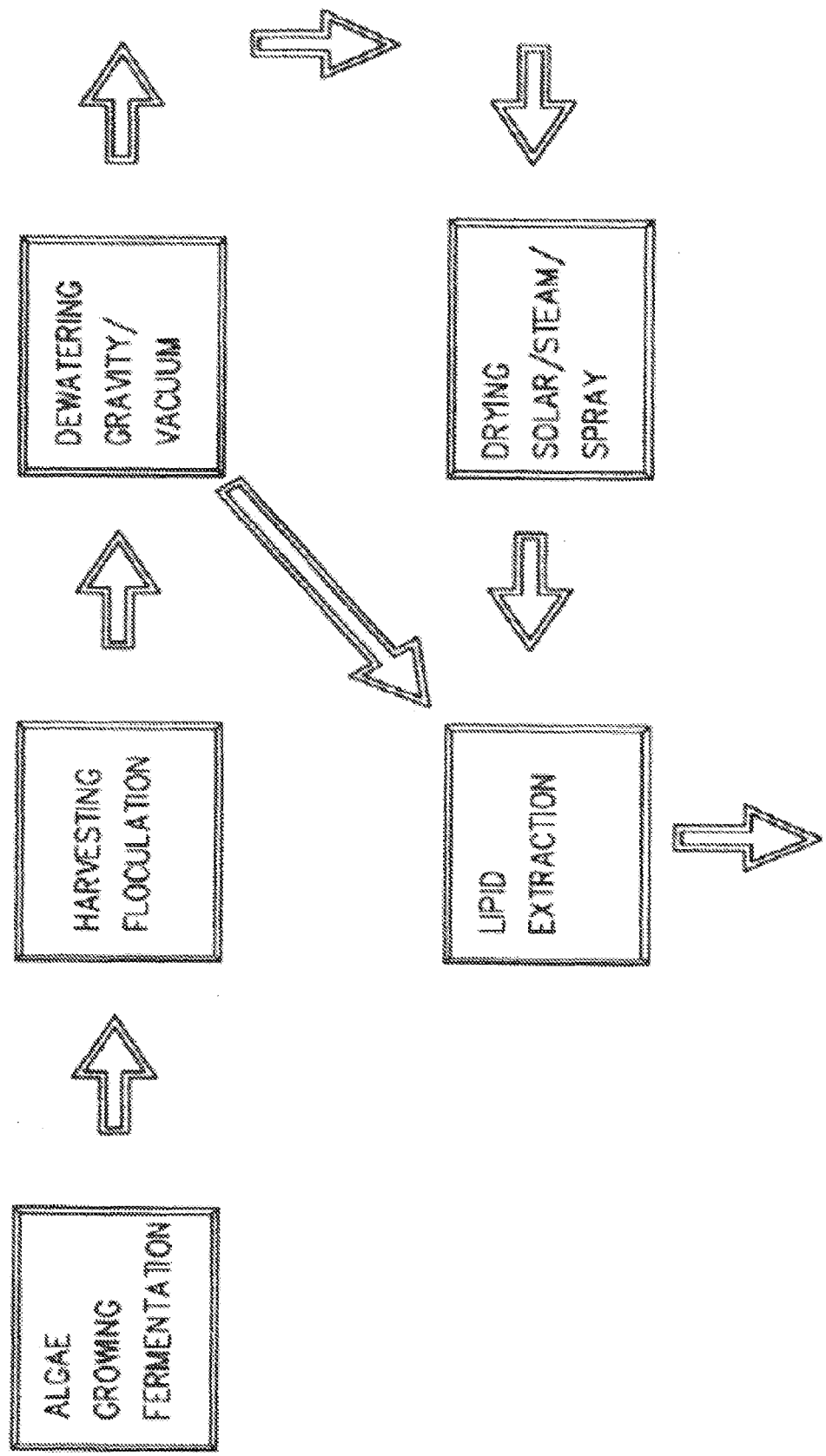
FIGURE 1. Algae Growing/Harvesting/Dewatering/Lipid Extraction System

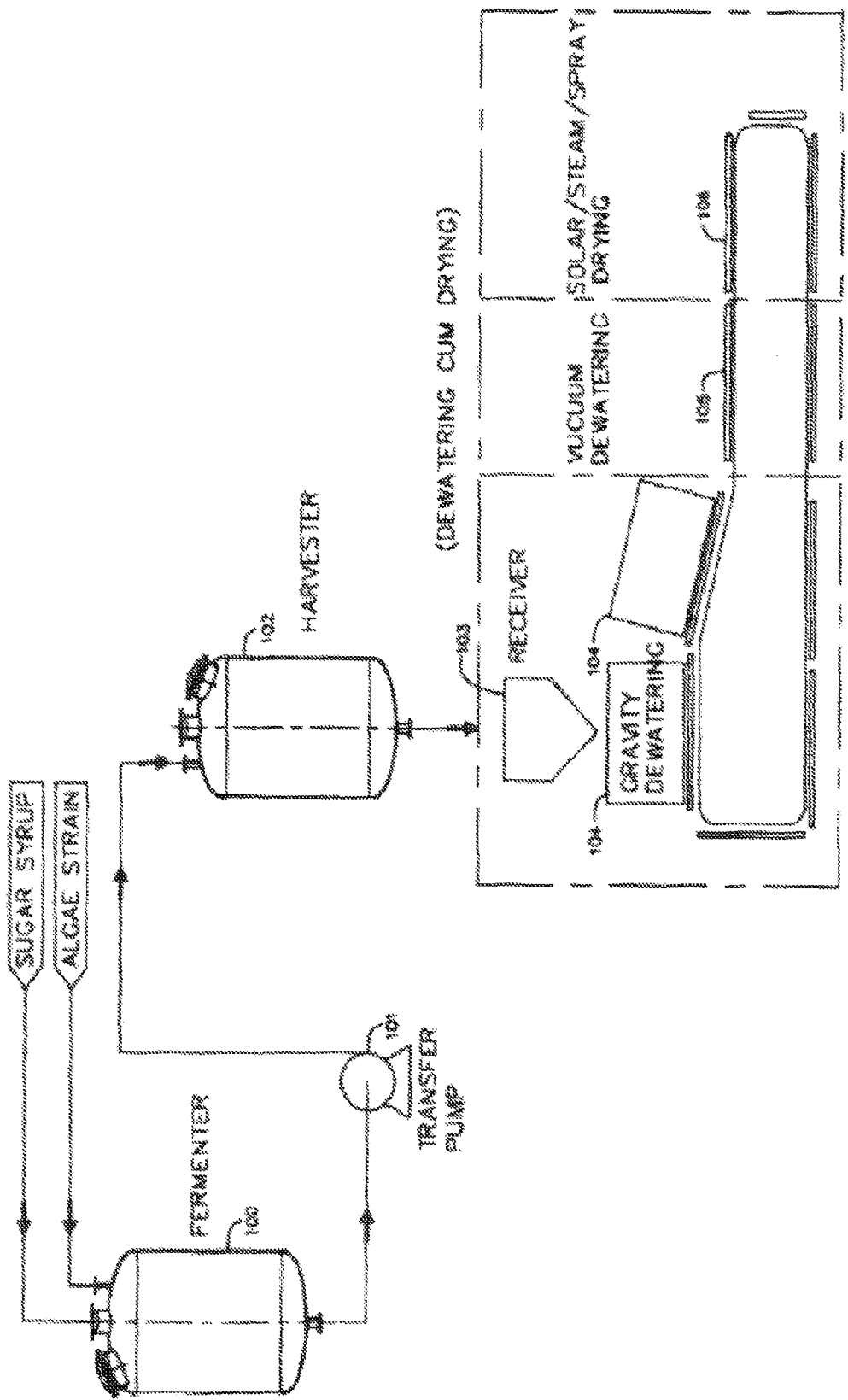
FIGURE 2. Fermenter/Harvester/Dewatering system

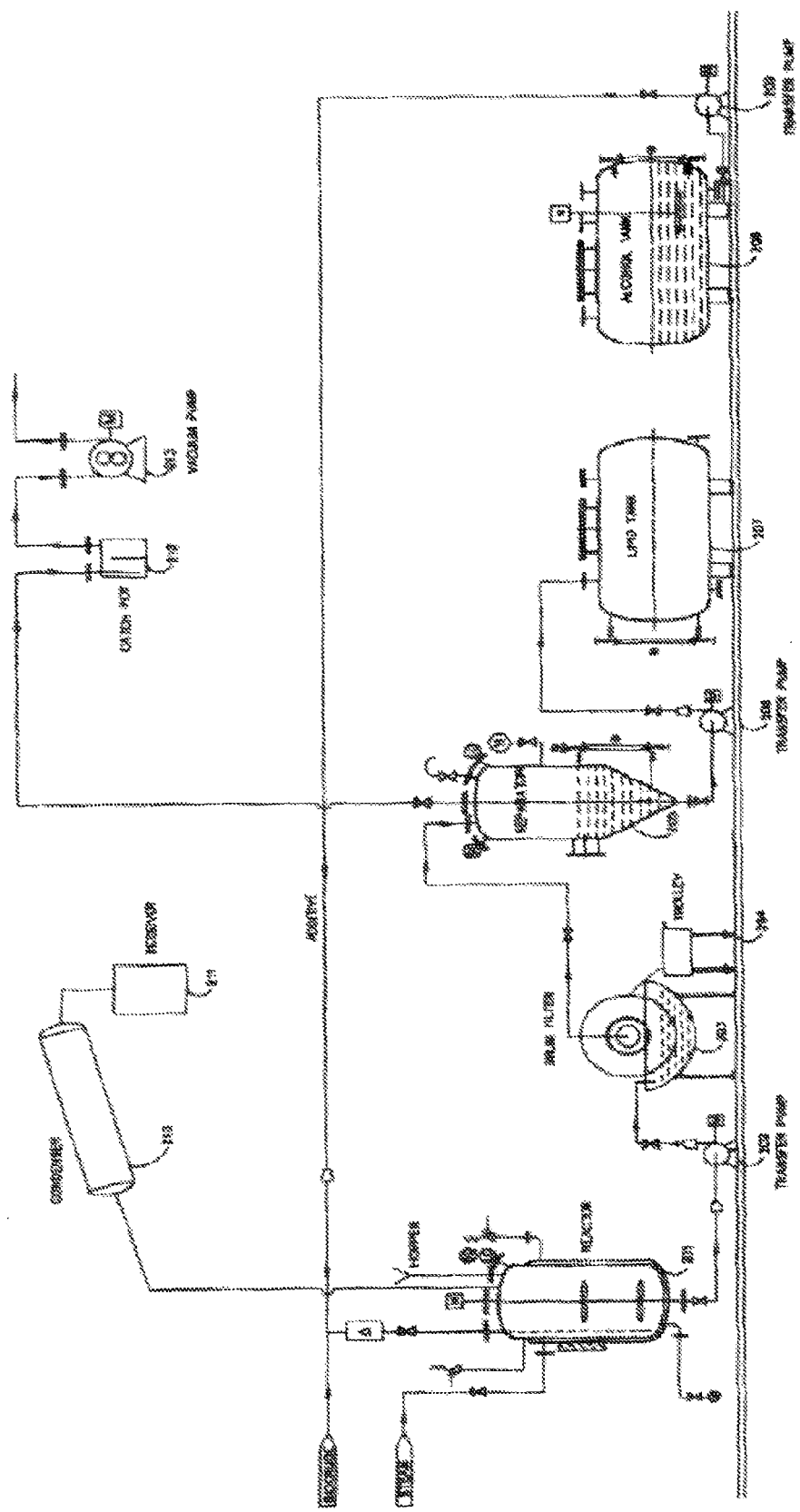
FIGURE 3. Lipid Extraction

METHODS FOR PRODUCTION OF ALGAE DERIVED OILS

CROSS-REFERENCE TO RELATED APPLICATIONS

This application claims priority under 35 U.S.C. §119(e) to U.S. Provisional Patent Application Ser. No. 61/354,367, filed on Jun. 14, 2010, which is incorporated herein by reference in its entirety, and also claims priority to International Application No. PCT/US2011/040320, filed Jun. 14, 2011, which is incorporated herein by reference in its entirety.

BACKGROUND OF THE INVENTION

1. Field of the Invention

The present invention is in the field of polyunsaturated fatty acid production and purification.

2. Description of the Related Art

An increase in healthcare costs and rising consumer knowledge of cardiovascular disease has caused an upsurge in consumer interest towards preventive healthcare. This scenario along with rising consumer knowledge about the health benefits of various foods and ingredients has triggered a transformation in the way consumers perceive food. An increasing number of consumers have started associating food with health and wellness, with many relying on nutritional supplements and fortified foods as an alternative means to prevent many health conditions. The growing number of highly informed consumers has also contributed to the development of a burgeoning functional foods market.

The functional foods market has evolved from merely fortified products offering generic health benefits to those that provide specific health benefits. This "new phase" of the functional foods market is largely supported by advancements in processing and nutraceutical technology, which have facilitated the introduction of novel products. With the demand for functional foods skyrocketing, the market is witnessing an influx of a wide array of products such as cereals, bread, beverages, eggs, dairy products, and convenience and processed foods that include various added supplements. Escalating consumer demand owing to rising self-care trends, staggering healthcare costs and overwhelming scientific evidence supporting functional ingredients have not just fueled the demand for functional foods, but have also generated considerable interest in dietary supplements. The increasing interest in nutritional supplements and functional foods has in turn paved the way for development of an attractive health ingredients market, particularly for ingredients with sound scientific support such as omega-3 ingredients.

Omega-3 ingredients are one of the most extensively researched and clinically established functional ingredients available in the food and beverage industry. Recently, omega-3 has emerged as a vital functional ingredient delivering significant health benefits, particularly those related to a healthy heart. The universal acceptance of the 'heart health' benefits of omega-3 oils can be ascribed to the enormous scientific evidence that has translated into rising consumer recognition (Kris-Etherton et al., Arteriosclerosis, Thrombosis, and Vascular Biology, 2003;23:151-152; Ruxton et al., Journal of Human Nutrition and Dietetics Volume 17, Issue 5, pages 449-459, October 2004). The total omega-3 PUFA (polyunsaturated fatty acid) ingredients market is witnessing a robust growth of 16.0% based on the ever-increasing demand for products containing omega-3 ingredients [March 2010 Frost and Sullivan report, "Strategic Analysis of the North American Marine and Algae Oil Omega-3 Ingredients Market"].

The omega-3 poly-unsaturated fatty acid (PUFA) ingredients market constitutes three different product categories, each with its unique characteristics, markets, and stages of development. The omega-3 ingredients are differentiated based on their source, which includes marine, algal, and flaxseed.

Sources

Fish is a major source of omega-3 PUFAs such as EPA and DHA. Flaxseed and algae serve as vegetarian sources of omega-3 fatty acids. While fish oils are a source of DHA and EPA, flaxseed serves as a source of ALA. EPA and DHA are long-chain omega-3 fatty acids that have well-established health benefits including lowering of triglyceride levels and reducing the risk of arrhythmia. However, ALA is a short-chain omega-3 fatty acid that is converted into EPA and DHA in the body. It has been observed that the conversion of ALA into the more useful longer-chain DHA and EPA in the body is not that efficient, specifically among the elderly. Hence, EPA and DHA derived from fish oils have a superior bioavailability as compared to other alternatives. The long-chain omega-3 PUFAs, DHA, and EPA are found in oily fish such as tuna, salmon, sardines, mackerel, and swordfish and in seaweed.

Algal oil is a concentrated source of DHA and accounted for 1.8 percent of the volume share in omega-3 fatty acids market in 2008 [March 2010 Frost and Sullivan report, "Strategic Analysis of the North American Marine and Algae Oil Omega-3 Ingredients Market"]. The established health benefits of DHA in brain and vision development of infants has led to its widespread use in infant nutrition market. Furthermore, it is increasingly being used in products that are developed specifically for pregnant women, infants and children. Presently, infant nutrition forms the largest application sector for algal oils, accounting for over 90.0% of the volume with the remainder used in dietary supplements and functional foods.

Recent developments indicating the nutritional and pharmaceutical importance of long chain omega-3 polyunsaturated fatty acids in the human diet have stimulated interest in micro algae as a source of these vital compounds, for they are the primary producers of these fatty acids in marine food webs. Food and pharmaceutical quality production can be enhanced both by the degree of process control and by the sterility achieved through a fermentation process (as compared to outdoor solar pond production). Existing data illustrate that micro algal-based heterotrophic production systems can exhibit omega-3 fatty acid productivities 2-3 orders of magnitude greater than those of outdoor pond systems. Additionally, long chain omega-3 fatty acid productivities reported for the micro algal fermentation systems are 1-2 orders of magnitude greater than productivities reported for fungal or bacterial systems. (Barclay et al., Journal of Applied Phycology, Vol. 6, No. 2, 123-129).

Selected fish oils are the main industrial sources of polyunsaturated fatty acids. However, this oil may be insufficient in the future to meet the expected growth in world demand for omega-3 fatty acids. Refined oils produced by marine micro algae represent a sustainable, renewable source of supplemental dietary fatty acids.

There are two main methods for algal production: Autotrophic (light and carbon dioxide as the source for sugar production) and heterotrophic (using external carbon sources such as sugars for energy). Autotrophic algae can be grown in open ponds or in bioreactors exposed to a light source. Heterotrophic algae are usually grown in closed bioreactors. For algae derived food products, heterotrophic growth represents a controlled, closed system less likely to be contaminated. However, closed reactor growth for the production of algae-derived omega-3 remains a capital-intensive system.

There remains a need in the industry for a renewable, sustainable source of nutritional ingredients such as omega-3. Alga is the answer if production costs can be lowered.

The present invention comprises a low cost method of growing heterotrophic algae using waste sugar as the energy source. This method cuts down the cost of heterotrophic growth of algae capable of producing significant amounts of omega-3 fatty acids by providing waste sugar as the nutrient source.

Furthermore, the present invention comprises a low cost, highly efficient dewatering method to remove a significant amount of water from algae for further processing; to date, dewatering has also been capital-intensive.

The present invention comprises a low cost, highly efficient method of extracting PUFAs without the use of hexane; to date, extraction of PUFAs has also been capital-intensive.

SUMMARY OF THE INVENTION

The present invention comprises a method of growing heterotrophic algae using sugar waste as the carbon source to produce polyunsaturated fatty acids including but not limited to omega-3.

The present invention comprises a method of dewatering biomass using a vacuum drum filtration system.

The present invention comprises a method of producing polyunsaturated fatty acids (PUFA) from a biomass containing PUFAs such as algae wherein the method does not utilize hexane and comprises the steps of: a) Growing algae in sugar supplemented growth media in closed bioreactors; b) Harvesting the biomass at optimal maximum densities ranging from 0.01 to 10% [dry weight/volume]; c) separating the biomass from the media; d) drying the filtered biomass; e) extracting total lipids by reacting the dried biomass with a suitable alcohol, and f) purifying polyunsaturated fatty acids from the total lipids. Harvesting may be enhanced by the addition of suitable flocculants such as modified starch. The biomass is then separated from the media by a vacuum drum filtration process. Filtered biomass can be further dried using one of several techniques including but not limited to oven drying, spray drying, and solar drying. The dried biomass can be used directly in various food and feed applications. The dried biomass can be further processed to obtain particular desirable compounds such as but not limited to omega-3, omega-6, vitamins, and pigments. A total lipid fraction from the biomass can be extracted by reacting with alcohol such as but not limited to methanol, ethanol, and butanol at a temperature ranging from 20 to 100° C. Lipids are concentrated by evaporating the solvent (alcohol) at 65 to 90° C. at 0.05 to 1 atmospheric pressure. Alcohol can be recovered by distillation. Specific polyunsaturated fatty acids such as but not limited to omega-3 can be purified from the total lipid fraction by standard procedures such as supercritical $CO_2$ extraction, cryo-phase separation, and acetone reaction.

Some embodiments include a system for producing algae compounds comprising: a growth reactor to facilitate growth of algae, a stress reactor to facilitate stress conditioning of algae, a dewatering system to produce a dried or semi-dry algae mass, a reaction chamber adapted to facilitate a reaction among the dried algae and an alcohol producing a reaction product comprising a first component comprising a lipid and a second component comprising algal bodies; and a vessel connected to the reaction chamber via a closable fluid connection. The growth of algae can comprise addition of nutrients, stirring, and adjustment of temperature and time. Stress conditioning of algae can comprise removal of a nutrient such as but not limited to nitrogen. The dewatering system can comprise a drum filtration unit. The reaction product can comprise a first component comprising a polyunsaturated fatty acid. The reaction product can comprise a second component comprising algal bodies. The alcohol can comprise at least one alcohol selected from methanol, ethanol, butanol, and hexanol. The vessel can comprise a separator adapted to facilitate recovery of alcohol from the reaction. The vessel can comprise a separator adapted to separate the lipids from the reaction. The extraction system can comprise a separator vessel, a lipid tank, and an alcohol tank.

A system for extracting total lipids from a biomass can comprise: a reaction chamber adapted to facilitate a reaction among a lipid-containing biomass and an alcohol to produce a reaction product comprising unreacted alcohol, a first component comprising PUFA, wherein the product can exit the reaction chamber through a port; a drum filtration unit connected to the reaction chamber to facilitate the removal of the solids from the reaction mixture; a separator connected to the drum filtration unit via a closable fluid connection, wherein the separator can be adapted to separate unreacted alcohol from the lipid fraction; a lipid tank connected to the separator via a closable fluid connection wherein the closable fluid connection can be adapted to permit the lipid fraction exiting the separator; an alcohol tank to store recovered unused alcohol; and a condenser and recovery unit connected to the alcohol tank.

BRIEF DESCRIPTION OF THE DRAWINGS

FIG. 1 depicts a schematic of the process of omega-3 production from algae.

FIG. 2 depicts the omega-3 production system comprising a Fermenter (100), Harvester (102), Receiver (103), Gravity Dewatering Filter Assembly (104), Vacuum Dewatering (105), Solar/Steam/Spray Drying (106). Fermenter receives sugar syrup and algae strain and other nutrients to produce algae culture. After a predetermined time, the algae culture is optionally moved to a stress reactor wherein one or more nutrients are provided in limited amount, thereby forcing the algae to produce a greater percentage of lipids. After a predetermined time, the algae culture is ready to be harvested. It is then transferred to a harvesting tank where optionally a flocculation agent is added to the Algae culture. After about 4 hours, the algae culture is released into the Receiver. Receiver transfers regulated quantity of flocculated algae and water to Gravity Dewatering Filter Assembly. After water drains out, filters flatten and go through a vacuum system that removes more water quantity. After vacuum dewatering, Filter Assembly moves to drying chamber which may employ Solar/Steam/Spray Drying methods known in the art. Water recovered from filtration process can be sent for processing before reuse/discharge.

FIG. 3 depicts a schematic of the Lipid Extraction system comprising a Reactor (201), Drum filter (203), Trolley (204), Separator (205), Lipid Tank (207), Alcohol Tank (208), Condenser (210), Receiver (211), Catch Pot (212), Vacuum Pump (213). Reactor is supplied with dry algae, suitable alcohol [1 volume of dry mass: 3 volumes of alcohol] and agitated at a suitable temperature and for a suitable amount of time to allow reaction to occur. Alcohol is recovered through distillation and Lipid with solid is transferred to a vacuum drum/belt. The drum filter removes solids [algae meal] for collection in Trolley and Lipid is transferred to a Separator. Lipid is heated to remove alcohol traces and then transferred to Lipid Tank.

DETAILED DESCRIPTION OF THE PREFERRED EMBODIMENT

The present invention comprises a method of polyunsaturated fatty acid (PUFA) production and purification from a PUFA containing biomass comprising the steps of a) growing the biomass in growth reactors or fermentors with a nutritional carbon source b) harvesting the biomass c) dewatering the biomass, and d) extracting total lipids from the biomass by adding alcohol and incubating for a time and at a temperature to allow sufficient mixing and separation of the mixture into an aqueous and organic phase, e) collecting the organic phase comprising total lipid and f) purifying PUFAs from the total lipid fraction.

The present invention comprises a method of PUFA production and purification from a biomass comprising the steps of a) growing the biomass in growth reactors or fermenters with a nutritional carbon source wherein the nutritional carbon source is derived from waste sugar, b) optionally moving the culture to different reactors for stress conditioning wherein the stress conditioning comprises nutrient limitation to increase oil production, c) harvesting the biomass d) dewatering the culture, e) extracting total lipid from the lipid containing biomass by adding alcohol, incubating for a time and at a temperature to allow sufficient mixing and separation of the mixture into an aqueous and organic phase, f) collecting the organic phase comprising total lipid, and g) extracting specific polyunsaturated fatty acids from the total lipids. The general process is described in FIG. 1.

The biomass that produces PUFAs can comprise algae, plant, yeast, or microorgamsms.

Harvesting lipid containing biomass may be achieved by a variety of methods including by not limited to flocculation, centrifugation, microscreens, centrifugation, flocculation, froth flotation, gravity filtration, vacuum drum filtration, vacuum flatbed filtration, and combinations thereof.

Dewatering biomass may be achieved by a variety of methods including but not limited to centrifugation, gravity filtration, vacuum drum filtration, vacuum flatbed filtration, and combinations thereof.

Algae Growth

The present invention comprises a method of growing heterotrophic algae in a closed bioreactor. This requires liquid media that include a carbon source such as sugar and various nutrients including but not limited to nitrogen, phosphorus, potassium and trace metals such as silica and iron. Various nutrition recipes are known in the art. However, for the production of high value ingredients such as but not limited to PUFAs, lowering the cost of production is essential for a viable production system. Therefore, any steps to lower growth costs would be beneficial. Some embodiments comprise a carbon source in the form of waste streams from com refineries, com syrup production systems, and com sugar.

Agriculture waste streams are gaining focus for recycling or minimization in order to improve the environment and limit human impact on it. Currently, there are a number of sugar waste sources in the agriculture industry that arise from the transportation of sugar from sources such as com, palm, and beet refineries. For instance, com syrups are shipped to various points in the USA by rail and, the railcars return to the source with approximately 2-3 percent of the original load stuck to the sides of vessel. Typically, this amounts to around 2-3 tons of 70% sugar per car. The current cleaning procedure involves washing the inside of the vessels with steam and discarding the effluent by shipping it to a wastewater treatment plant. This represents a significant cost center to the refiners as the waste represents unusable product and, the water that is used to wash the rail cars has to be transported for further treatment. As algae can be grown in 1% sugar, we propose to use this waste sugar water as one main ingredient for algae growth media. Instead of the waste sugar water being transported to a water treatment facility, it can be used to grow algae. Furthermore, since it comes in liquid format (water), one does not have to provide liquid media for growth. This represents another huge cost savings for algae growth. Another source of sugar waste is "off spec" sugars; this is sugar preparations that do not pass the QC specifications required for sale. Current estimates of this type of sugar in Lee County (Iowa) alone exceed millions of gallons per year.

The present invention comprises a method of growing algae in fermenter tanks using sugar waste as one component of the growth media. The algae are grown in the tanks for a sufficient time and at a temperature to promote accumulation of biomass. The algae can be harvested at this step or optionally, moved to stress tanks for accumulation of specific compounds or molecules.

The growth of lipid containing organisms can be performed at room temperature, at about 40° C., at about 60° C., at about 70° C., at about 80° C., at about 90° C., or at about 100° C. The growth of lipid containing organisms can be performed for a sufficient time to accumulate biomass. A sufficient time to accumulate biomass can include about 6 hours, about 18 hours, about 24 hours, about 36 hours, about 48 hours, about 60 hours, about 72 hours, or more than 72 hours.

Stress Conditions

Algae can accumulate specific compounds or molecules when exposed to stress conditions including but are not limited to nutrient limitation, temperature, or pH changes. It is known that nitrogen limitation can lead to lipid accumulation in certain strains of algae. In fact, there are particular strains that exhibit greater omega-3 production under nitrogen limitation (Ward et al., Appl. Environ. Microbio., February 1991 p. 419-425; Reitan et al., J. Phycology, December 1994, Vol. 30, Issue 6, pp. 972-979).

The present invention comprises the optional step of stress conditioning wherein the step comprises moving the algae from growth fermentor tanks to stress tanks in which the algae culture is subjected to particular stress conditions such as but not limited to nitrogen limitation, nitrogen excess, temperature change, pH change, and carbon source limitation. The present invention comprises the step of stress conditioning wherein the stress condition comprises nitrogen limitation.

The stress conditioning of lipid containing organisms can be performed at room temperature, at about 40° C., at about 60° C., at about 70° C., at about 80° C., at about 90° C., or at about 100° C. The stress of lipid containing organisms can be performed for a sufficient time to accumulate lipid. A sufficient time to accumulate lipid can include about 6 hours, about 18 hours, about 24 hours, about 36 hours, about 48 hours, about 60 hours, about 72 hours, or more than 72 hours.

Harvest/Dewater

After growth and/or stress conditioning of algae, the algae is harvested and dewatered. There are a number of methods known in the art including but not limited to flocculation, centrifugation, microscreens, centrifugation, flocculation and froth flotation. Interrupting the carbon dioxide supply can cause algae to flocculate on its own, auto flocculation. Chitosan, alum and ferric chloride are chemical flocculants (Mater, 2009 Dec. 15; 172 (1):38-45). In froth flotation, the cultivator aerates the water into froth, and then skims the algae from the top.

Another aspect of the present invention that provides further cost reduction in algae growth is the highly efficient dewatering method of the instant invention. As shown in FIG. 2, the harvesting/dewatering system can comprise a vacuum drum filtration unit (Gravity Dewatering Filter Apparatus). Embodiments of the present invention comprise subjecting biomass containing fluid to a drum filter with four segments, namely vacuum zone, neutral zone, purge zone, and harvesting zone. The drum is covered with a micro-membrane that allows selective collection of micro algae on the membrane while the culture media is collected for disposal or reuse. The method allows the recovery of algae at 20-30% dry mass After water drains out, the biomass is filtered, flattened and goes through a vacuum system which removes some more water quantity.

The dewatered algae can be further dried using any number of processes known in the art including but not limited to spray drying, indirect heat, fluid bed, dirt heat, and microwaving. The dewatered biomass moves to a drying chamber, which may employ solar, steam, or spray drying methods. Water recovered from filtration process can be further processed before reuse/discharge. The dried algae meal can be further processed for purification of specific components, such as but not limited to oils, amino acids, and pigments.

Optionally, the dried meal can be used as an additive in a number of products including but not limited to animal feed, pet food, aqua feed, and other similar products. There is currently a high demand for algae meal as it is a good source of protein.

Total Lipid Extraction

Another aspect of the present invention that provides further cost reduction in algae processing is the highly efficient extraction method of the instant invention. The present invention provides a low cost method of extracting total lipids (without tremendous energy input) from which specific PUFAs are isolated and purified.

The extraction system is flexible, scaleable, and does not require extreme pressure, temperature, or corrosive reagents. The reaction utilizes alcohol. The reaction is capable of processing 2000 Kg of dewatered algae, which in turn produces 400 Gallons of total lipid. The reactants can be used up to four times before the spent reactants are sent to a distillation tower for recovery of the ethanol fraction. The re-use and distillation steps enable the system to have a total of at least 90% recovery of alcohol, further enabling a cost saving process. Merely by way of example, dried algae is mixed with 1-3 volumes of methanol and heated at 65° C. for 1 hour and subjected to vacuum drum filtration. The filtrate comprising total lipids is subjected to distillation at 80° C. where methanol was collected by condensation; the residual material comprising total lipids is subjected to acetone extraction, supercritical $CO_2$ extraction, or cryo-phase separation for concentrating omega-3.

The process for extracting lipids from a biomass can include contacting the reaction agents comprising the biomass and an alcohol. The contacting can comprise mixing. The mixing can be performed by a mechanical mixer, a vibrator, a circulating pump, a sonicator, or the like, or a combination of.

The contacting can be performed at room temperature. The contacting can be performed at a temperature other than room temperature. The contacting can be performed at about 0° C., at about 10° C., at about 20° C., at about 30° C., at about 40° C., at about 60° C. at about 70° C., at about 80° C., at about 90° C., at about 100° C., at about 110° C., at about 120° C., or at a temperature higher than at about 120° C. The contacting can be performed within a temperature range of at about ±0° C., at about ±2° C., at about ±5° C., at about ±10° C., at about ±15° C., at about ±20° C., at about ±25° C., at about ±30° C., at about ±35° C., at about ±40° C., at about ±45° C., or at about ±50° C., or higher. The contacting can be performed at about a temperature about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 115S%, about 120%, or higher than about 120% of the boiling point of the alcohol. The contacting can be performed at a fixed temperature. The contacting can be performed at a temperature varying during the contacting.

The contacting can be performed at about atmospheric pressure. The contacting can be performed at a pressure higher than atmospheric pressure. The contacting can be performed about 100%, or about 110%, or about 120%, or about 150%, or about 200%, or about 250%, or about 300%, or about 400%, or about 500%, or about higher than 500% of atmospheric pressure. The contacting can be done at lower than atmospheric pressure. The contacting can be performed at about 10%, at about 20%, at about 30%, at about 40%, at about 50%, at about 60%, at about 70%, at about 80%, or about 90% of atmospheric pressure.

The mixing can be performed by a pre-selected mixing parameter including duration, strength, frequency, or the like, or a combination thereof.

The lipid extraction system can include a reaction chamber. The reaction chamber can include a reaction vessel or container of any suitable volume, for example, smaller than 1 mL, from about 1 mL to about 100 mL, from about 100 mL to about 250 mL, from about 250 mL to about 500 mL, from about 500 mL to about 1 Liter, from about 1 L to 10 L, from about 10 L to 100 L, from about 100 L to 250 L, from about 250 L to about 500 L, from about 500 L to about 1000 L, from about 1000 L to about 5000 L, from about 5000 L to about 10,000 L, from about 10,000 L to about 50,000 L, from about 50,000 L to about 100,000 L, from about 100,000 L to about 250,000 L, or larger than 250,000 L.

The contact can result in the formation of a reaction product comprising a first component comprising lipid. The first component can be further processed to purify PUFAs such as but not limited to omega-3. The reaction product can include at least a second product comprising biomass solids. The biomass solids can comprise algal bodies, protein, and/or carbohydrates. The PUFAs can be used as a food additive, food supplement, or food ingredient. The biomass solids can be used as a food additive, food supplement, or food ingredient.

A byproduct of the lipid extraction process is de-fatted algae meal. This too can be used as an additive in a number of products such as but not limited to animal feed, pet food, aquaculture feed, and other similar products. There is currently a high demand for algae meal that has been de-fatted as it is a source of protein.

The extraction process can include separating unreacted alcohol from the reaction product. The separation of the unreacted alcohol from the reaction product can be performed by, for example, fractional distillation. Merely by way of example, the reaction product comprising unreacted alcohol can be distilled to recover unreacted alcohol. The distillation can be performed at a temperature of from about 20° C. to about 200° C., from about 30° C. to about 150° C., from about 40° C. to about 120° C., from about 50° C. to about 100° C., from about 60° C. to about 90° C., or from about 70° C. to about 80° C. The distillation can be performed at a pressure from about 0.1 atmospheric pressure to about 10 atmospheric pressure, from about 0.2 atmospheric pressure to about 8 atmospheric pressure, from about 0.5 atmospheric pressure to about 5 atmospheric pressure, from about 0.8 atmospheric pressure to about 3 atmospheric pressure, from about 0.6 atmospheric pressure to about 2 atmospheric pressure, from about 0.7 atmospheric pressure to about 1.5 atmospheric pressure, from about 0.8 atmospheric pressure to about 1.2 atmospheric pressure, or about 1 atmospheric pressure. The unreacted alcohol separated from the reaction can be collected. The unreacted alcohol separated from the reaction product can be reused in the extraction process, or in some other processes.

The reaction product comprising a first component comprising a lipid can be separated from biomass solids by methods including but not limited to vacuum drum filtration. The lipid can be collected in a lipid tank.

PUFA Purification

When purifying PUFAs from the total lipid fraction, omega-3 is purified by any standard method including but not limited to supercritical $CO_2$ extraction (Follegatti-Romero et al., J. of Supercritical Fluids, July 2009; 49 (3):323-329), cryo-phase separation, and acetone reaction.

Example 1

For the extraction of lipids from a dried biomass, 25 kilograms of dried algae is loaded to the reaction vessel followed by 50 kilograms of ethanol. The reactor is heated to 80° C. with constant stirring. After one (1) hour, the heater is turned off and the reaction is allowed to cool to 45° C. The mixture is passed through a vacuum drum filter where the solids are separated from the liquid. The liquid containing total lipids were evaporated to dryness under vacuum and the residue was dissolved in 1 liter of acetone. The acetone fraction was subjected to evaporation under nitrogen and the PUFA enriched residue was collected.

The invention claimed is:

1. A process for producing algae derived omega-3 comprising:
   a. growing heterotrophic algae in media comprising heat-sterilized waste water containing sugar for a sufficient time to create an algae culture;
   b. harvesting the algae;
   c. dewatering the algae to produce an algae biomass that is substantially dried using a vacuum filtration unit comprising:
      i. at least one collapsible gravity dewatering filter assembly comprising a filter that is permeable to water and substantially impermeable to algae biomass, and further comprising collapsible sides connected to said filter, said filter and said sides at least partially define a volume there between, such that the filter assembly is configured to contain a regulated quantity of algae and water in a gravity dewatering zone, and further wherein the sides of the filter assembly collapse after at least a portion of the water is removed from the algae by gravity dewatering;
      ii. a vacuum zone that receives the filter assembly with collapsed sides and further separates the water from the algae; and
      iii. a drying zone;
      wherein the filter assembly moves between each zone;
   d. extracting total lipid from the dried biomass without the use of hexane, said extracting step comprising:
      i. adding ethanol to said dried biomass to make an ethanol-biomass mixture;
      ii. incubating the ethanol-biomass mixture between about 60° C. and about 80° C. for a time to allow extraction of the total lipid from the biomass;
      iii. collecting the ethanol and total lipid; and
      iv. separating a total lipid fraction from the ethanol; and
   e. purifying omega-3 from the total lipid fraction.

2. The process of claim 1, further comprising stressing the algae by subjecting the culture to nutrient limitation prior to step (b).

3. The process of claim 1 wherein harvesting the algae comprises a method selected from flocculation, centrifugation, microscreens, froth flotation, and combinations thereof.

4. The process of claim 1, wherein the separating step is performed in a separator capable of facilitating separation of the lipid fraction from solids, and the lipid fraction is subsequently moved to a lipid tank.

5. The process of claim 1 wherein purifying omega-3 from the total lipid fraction is selected from the methods of supercritical CO2 purification, cryo-precipitation, and acetone purification, and wherein said purifying involves treatment of the total lipid fraction of claim 1 with reagents consisting of a coolant and either CO2 or acetone.

6. The process of claim 1 wherein the algae are dried to a 20-30% dry mass.

7. The method of claim 1, wherein the ethanol is recovered and reused.

8. The method of claim 1, further comprising collecting the biomass after step (d)(ii).

9. The method of claim 8, further comprising processing the biomass for purification of oils, amino acids, and/or pigments.

10. The method of claim 8, wherein the biomass is processed for use as an additive in animal feed, pet food, and/or aqua feed.

11. The method of claim 1, wherein the algae remains associated with the filter in the vacuum zone.

* * * * *